US00PP10820P

United States Patent [19]

Pouw

[11] Patent Number: Plant 10,820

[45] Date of Patent: Mar. 9, 1999

[54] MINIATURE ROSE PLANT NAMED 'RUIMATS'

[75] Inventor: Antonius A. Pouw, De Kwakel, Netherlands

[73] Assignee: De Ruiter's Nieuwe Rozen B.V., De Kwakel, Netherlands

[21] Appl. No.: 887,985

[22] Filed: Jul. 3, 1997

[51] Int. Cl.[6] ..... A01H 5/00

[52] U.S. Cl. ..... Plt./10

[58] Field of Search ..... Plt./10.1, 10

*Primary Examiner*—Howard J. Locker
*Attorney, Agent, or Firm*—C. A. Whealy

[57] ABSTRACT

A distinctive cultivar of miniature rose plant named 'Ruimats', characterized by its very large dark orange/red flowers with numerous petals; dark green leaves; vigorous growth habit; strong rooting habit; exceptional postproduction longevity; and excellent garden performance.

2 Drawing Sheets

The present invention relates to a new and distinct cultivar of the miniature rose class, botanically known as *Rosa hybrida,* and hereinafter referred to by the cultivar name Ruimats. The new cultivar will be marketed under the trade name Optima Orange.

The new cultivar is a product of a planned breeding program conducted by the inventor in Hazerswoude, The Netherlands. The objective of the breeding program was to develop pot rose varieties with novel and attractive flower colors and excellent postproduction longevity and garden performance. The new cultivar originated from a cross made by the inventor in 1992 of two unnamed proprietary seedlings. The cultivar Ruimats was discovered and selected by the inventor as a flowering plant within the progeny of the stated cross in a controlled environment in Hazerswoude, The Netherlands.

Asexual reproduction of the new cultivar by cuttings taken at Hazerswoude, The Netherlands, has shown that the unique features of this new miniature rose plant are stable and reproduced true to type in successive generations of asexual reproduction.

The following traits have been repeatedly observed and are determined to be the unique characteristics of 'Ruimats'. These characteristics in combination distinguish the new miniature rose plant as a new and distinct cultivar:

1. Very large dark orange/red flowers with numerous petals.
2. Dark green leaves.
3. Vigorous growth habit.
4. Strong rooting habit.
5. Exceptional postproduction longevity.
6. Excellent garden performance.

The new miniature rose plant has not been observed under all possible environmental conditions. The phenotype may vary significantly with variations in environment such as temperature and light level, without, however, any variance in genotype.

BRIEF DESCRIPTION OF PHOTOGRAPHS

The accompanying colored photographs illustrate typical specimens of the vegetative growth and flowers of the new miniature rose plant, showing the colors as true as it is reasonably possible to obtain in colored reproductions of this type.

The photograph on the first sheet comprises a top perspective view of a typical plant of the new miniature rose plant grown in. Hazerswoude, The Netherlands.

The photograph on the second sheet comprises details of the new miniature rose plant. In this photograph the apex of a young shoot (1); a leaf with three leaflets (2); a leaf with five leaflets (3); a leaf with seven leaflets (4); a stem without leaves (5); a flower bud after sepals open (6); a flower bud after petals begin to unfurl (7); a flower one-half open (8); and a flower fully open (9); a flower stem with sepals, stamens and pistils (10); a flower stem with sepals and pistils (11); and a flower stem with pistils only (12) are shown. Flower and foliage color in these photographs may appear different from the actual colors due to light reflectance.

DETAILED BOTANICAL DESCRIPTION

The following observations, measurements, values, and comparisons describe plants grown in Hazerswoude, The Netherlands, under glass covering with average day temperatures of 20° C., average night temperatures of 16° to 18° C., and an average light level of 2,000 J/cm$^2$.

In the following description, color references are made to The Royal Horticultural Society Colour Chart except where general terms of ordinary dictionary significance are used.

Classification:

*Botanical.*—*Rosa hybrida* cultivar Ruimats.

*Commercial.*—Miniature pot rose.

Parentage:

*Male or pollen parent.*—Unnamed proprietary seedling.

*Female or seed parent.*—Unnamed proprietary seedling.

Propagation:

*Type.*—Terminal or stem cuttings.

*Time to rooting.*—8 to 10 days with soil temperatures of 20° C.

*Rooting habit.*—Propagates easily, roots strong and well-branched.

Plant description:

*Form.*—Rounded form, uniform, and spreading.

*Growth habit.*—Vigorous. Freely branching and dense growth. Suitable for 12-cm and larger containers. Time to produce a finished plant in a 12-cm container 20 to 30 cm in height and 15 to 20 cm in width is generally 12 to 14 weeks depending on average temperature, light level, and cultural practices.

*Stem and lateral branches.*—Quantity of lateral branches from pinching: Typically three. Length of lateral branches: 1 to 5 cm. Diameter of lateral branches: 1 to 2 mm. Internode length: 1.5 to 2.5 cm. Color: 137B.

*Foliage description.*—Leaves arranged alternately, compound with three to seven leaflets per leaf, generally symmetrical, abundant, and flat in aspect. Stipules at petiole base. Quantity of leaves: Five to eight per lateral branch. Leaflet length: 2.5 to 3.5 cm. Leaflet width: About 1.6 cm. Shape: Ovate with acute apex and obtuse base. Margin: Serrate. Texture: Smooth and leathery. Petiole length: 1.5 to 2 cm. Petiole diameter: About 1 mm. Color: Young foliage, upper side: 137C. Young foliage, under side: 137D with narrow, 60B, margins. Mature foliage, upper side: 137A with 60B margins. Reddish margins more obvious on plants exposed to high light conditions. Mature foliage, under side: 137B. Petiole: 138B.

*Prickles.*—Sparse. Length: About 1 mm. Color: 138D.

Flower description:

*Flower type and habit.*—Very large dark orange/red flowers with numerous petals. Consistently symmetrical rosette flowers that are flat in aspect. Freely and continuously flowering. The flowers are borne singly on peduncles with usually one to two flowers per lateral stem. Petals persistent.

*Flowering season.*—Year-round under greenhouse conditions, optimal flowering from spring through autumn under garden conditions.

*Flower diameter.*—About 4 cm.

*Flower depth (height).*—About 1.4 cm.

*Flower longevity on plant.*—About 25 days.

*Fragrance.*—Absent.

*Flower buds.*—Shape: Ovoid. Length: 0.6 to 2 cm. Diameter: 5 to 8 mm. Color: 137C.

*Petals.*—Quantity: 40 to 50 per flower. Typically eight or ten rows with five petals each. Length: About 2 cm. Width: 1 to 1.8 cm. Shape: Rounded with obtuse apex. Margin: Entire. Texture: Smooth and satiny. Color: Upper side, when opening: 45A at apex, 44A at center, white at base. Under side, when opening: 45B with white at base. Upper side, fully opened: 44B with white at base. Under side, fully opened: 44C with white at base. Fade: Flower color does not fade.

*Petaloids.*—Quantity: About 15 per flower. Arrangement: About three rows of five petaloids. Length: 0.8 to 1.2 cm. Width: 4 to 7 mm. Margin: Entire. Texture: Smooth and satiny. Color: Immature: 44B with white stripe. Mature: 44B with white base.

*Sepals.*—Quantity: Typically five per flower. Shape: Narrowly ovate with acute tip. Texture: Pubescent. Color: Upper side: 144A with 144B at base. Under side: 137A at apex with 137C at center and 144B at base.

*Calyx.*—Length 6 to 7 mm. Diameter: 5 to 6 mm. Shape: Funnel.

*Peduncles.*—Strength: High. Aspect: Erect. Length: 2 to 4.5 cm. Color: 137C.

*Reproductive organs.*—Stamens: Quantity: 60 to 70 per flower. Anther size: About 2 mm. Anther shape: Oblong. Anther color: 22B. Pistils: Quantity: About 20 per flower. Style length: 8 to 9 mm. Style color: 145C.

Disease resistance: Plants appear to be relatively tolerant to Powdery Mildew.

Seed production: Seed production is rarely observed.

It is claimed:

1. A new and distinct miniature rose plant named 'Ruimats', as illustrated and described.

* * * * *

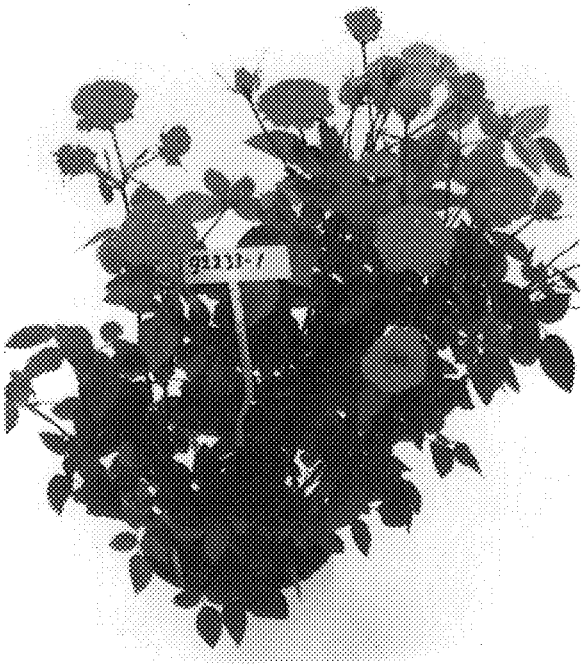

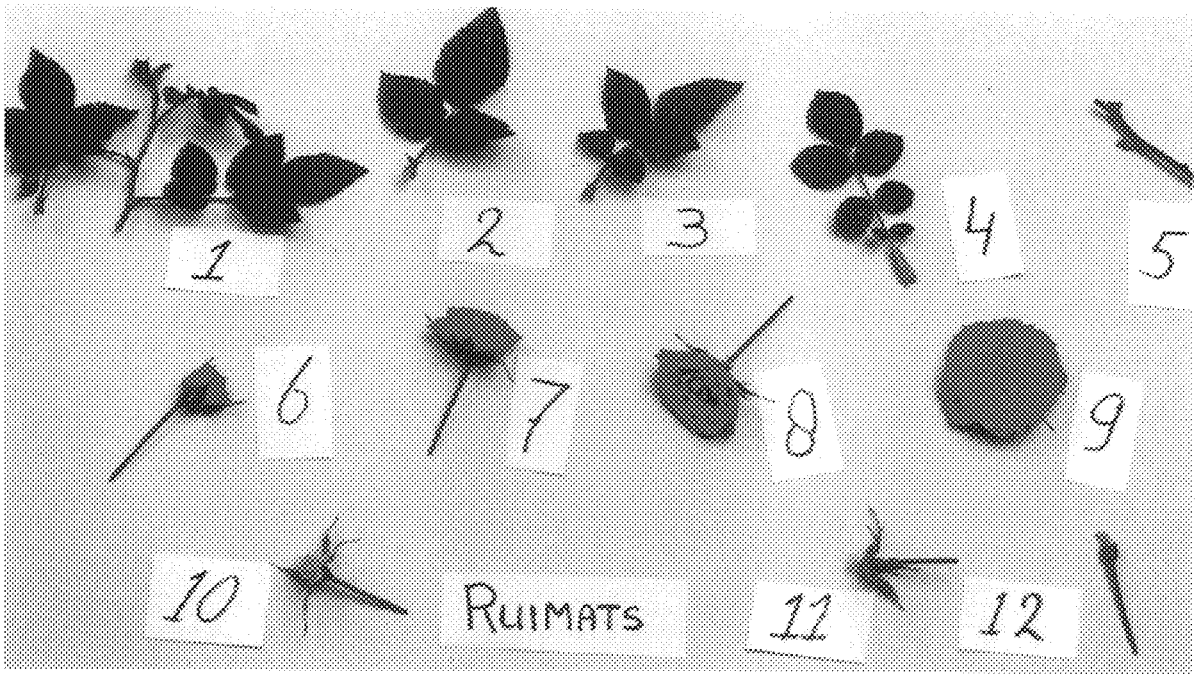
1
2
3
4
5
6
7
8
9
10
RUIMATS
11
12